(12) United States Patent
Palmqvist et al.

(10) Patent No.: US 11,033,442 B2
(45) Date of Patent: Jun. 15, 2021

(54) PACKAGING UNIT FOR HYGIENE ARTICLES

(71) Applicant: Essity Hygiene and Health Aktiebolag, Gothenburg (SE)

(72) Inventors: Lisa Palmqvist, Gothenburg (SE); Sara Hagberg, Mölndal (SE); Annika Dahl, Gothenburg (SE); Sofia Ekstedt, Gothenburg (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 0 days.

(21) Appl. No.: 16/640,551

(22) PCT Filed: Aug. 22, 2017

(86) PCT No.: PCT/SE2017/050843
§ 371 (c)(1),
(2) Date: Feb. 20, 2020

(87) PCT Pub. No.: WO2019/039979
PCT Pub. Date: Feb. 28, 2019

(65) Prior Publication Data
US 2020/0383848 A1 Dec. 10, 2020

(51) Int. Cl.
*A61F 13/551* (2006.01)
*C09J 7/22* (2018.01)
(Continued)

(52) U.S. Cl.
CPC .... *A61F 13/5514* (2013.01); *A61F 13/15739* (2013.01); *A61F 13/15747* (2013.01);
(Continued)

(58) Field of Classification Search
CPC ............ A61F 13/5514; A61F 13/15739; A61F 13/15747; C09J 7/22; C09J 7/30;
(Continued)

(56) References Cited

U.S. PATENT DOCUMENTS

| 4,186,743 A | 2/1980 | Steiger |
| 4,832,507 A | 5/1989 | Herrington |

(Continued)

FOREIGN PATENT DOCUMENTS

| CN | 104244894 A | 12/2014 |
| CN | 105658190 A | 6/2016 |

(Continued)

OTHER PUBLICATIONS

International Search Report and Written Opinion for International Application No. PCT/SE2017/050843, dated Mar. 21, 2018, 10 pages.

(Continued)

*Primary Examiner* — Patricia L. Nordmeyer
(74) *Attorney, Agent, or Firm* — Wood Herron & Evans LLP

(57) ABSTRACT

A packaging unit for hygiene articles and a method for producing the same. The packaging unit is formed from a sheet of material having an inner surface and an outer surface. The inner surface has an edge zone. The sheet has at least one folding axis and the folding axis divides the sheet into a first region and a second region. The sheet may be folded along the folding axes with the first and second regions in an overlapping configuration, and at least a part of the edge zone is provided with microencapsulated adhesive.

18 Claims, 5 Drawing Sheets

(51) Int. Cl.
*C09J 7/30* (2018.01)
*A61F 13/15* (2006.01)
*B65D 65/14* (2006.01)
*B65D 75/20* (2006.01)
*B65D 75/04* (2006.01)
*B65D 75/26* (2006.01)

(52) U.S. Cl.
CPC ............ *A61F 13/551* (2013.01); *B65D 65/14* (2013.01); *B65D 75/20* (2013.01); *C09J 7/22* (2018.01); *C09J 7/30* (2018.01); *A61F 13/15707* (2013.01); *A61F 13/5513* (2013.01); *B65D 75/04* (2013.01); *B65D 75/26* (2013.01); *C09J 2301/204* (2020.08); *C09J 2301/412* (2020.08); *Y10T 428/28* (2015.01); *Y10T 428/2813* (2015.01); *Y10T 428/2817* (2015.01)

(58) Field of Classification Search
CPC .......... C09J 2301/412; C09J 2301/204; B65D 65/14; B65D 75/20; Y10T 428/28; Y10T 428/2813; Y10T 428/2817
See application file for complete search history.

(56) References Cited

U.S. PATENT DOCUMENTS

| | | | |
|---|---|---|---|
| 5,709,340 A | 1/1998 | Chao | |
| 6,209,779 B1 * | 4/2001 | Fabel | B42D 15/08 229/301 |
| 6,370,804 B1 * | 4/2002 | Truc | G03B 21/64 40/702 |
| 6,375,872 B1 | 4/2002 | Chao | |
| 2005/0092440 A1 * | 5/2005 | Lindsay | B65H 45/144 156/442.1 |

FOREIGN PATENT DOCUMENTS

| | | |
|---|---|---|
| CN | 105682630 A | 6/2016 |
| CN | 106413656 A | 2/2017 |
| CN | 106535851 A | 3/2017 |
| FR | 2699833 B1 | 8/1995 |
| GB | 2412904 A | 10/2005 |
| JP | 02102280 A | 4/1990 |
| JP | H02102280 A | 4/1990 |
| JP | 2014201649 A | 10/2014 |
| WO | 2013031647 A1 | 3/2013 |
| WO | 2013162430 A1 | 10/2013 |
| WO | 2015060770 A1 | 4/2015 |
| WO | 2015190969 A1 | 12/2015 |
| WO | 2015190970 A1 | 12/2015 |

OTHER PUBLICATIONS

International Preliminary Report on Patentability and Written Opinion for International Application No. PCT/SE2017/050843, dated Feb. 25, 2020, 6 pages.
National Intellectual Property Administration (CNIPA) of the People's Republic of China, Notification of the Frist Office Action in CN Application No. 201780093217.3, dated Jul. 9, 2020 (13 pages).
Russian Patent Office (Federal Service for Intellectual Property (Rospatent)), Decision to Grant issued in RU Application No. 2020111553/03(019512), dated Jun. 22, 2020 (17 pages).
European Patent Office, Extended Search Report issued in EP 17922398.7-1102, dated Mar. 11, 2021, 5 pages.

* cited by examiner

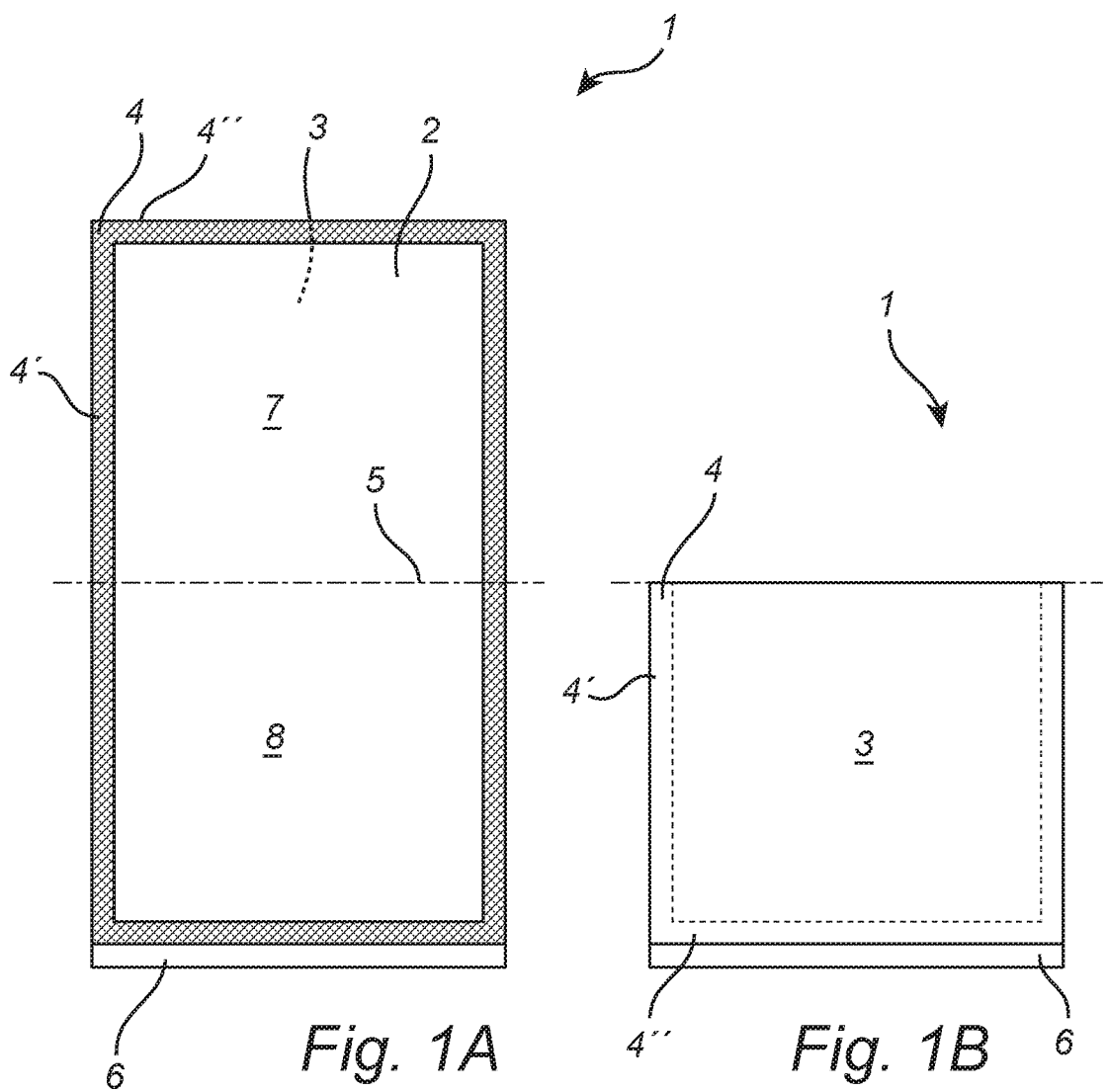
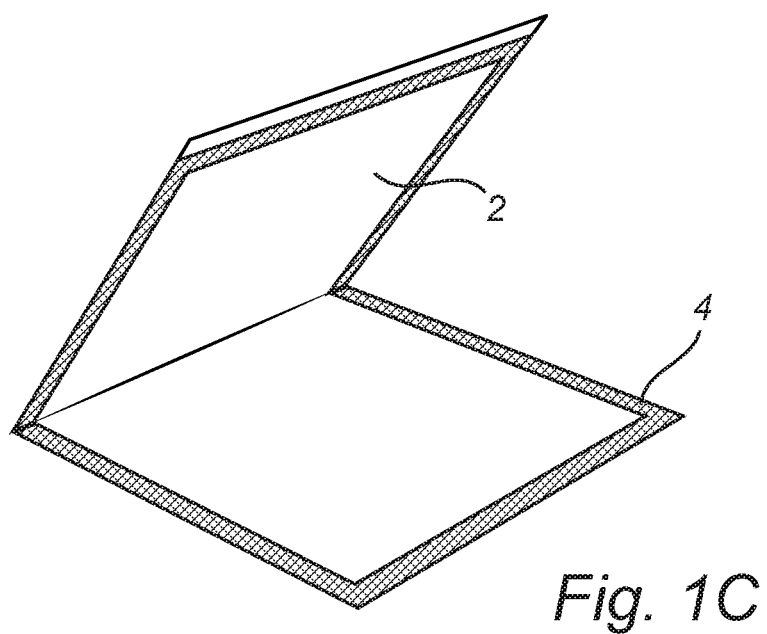
Fig. 1A Fig. 1B
Fig. 1C

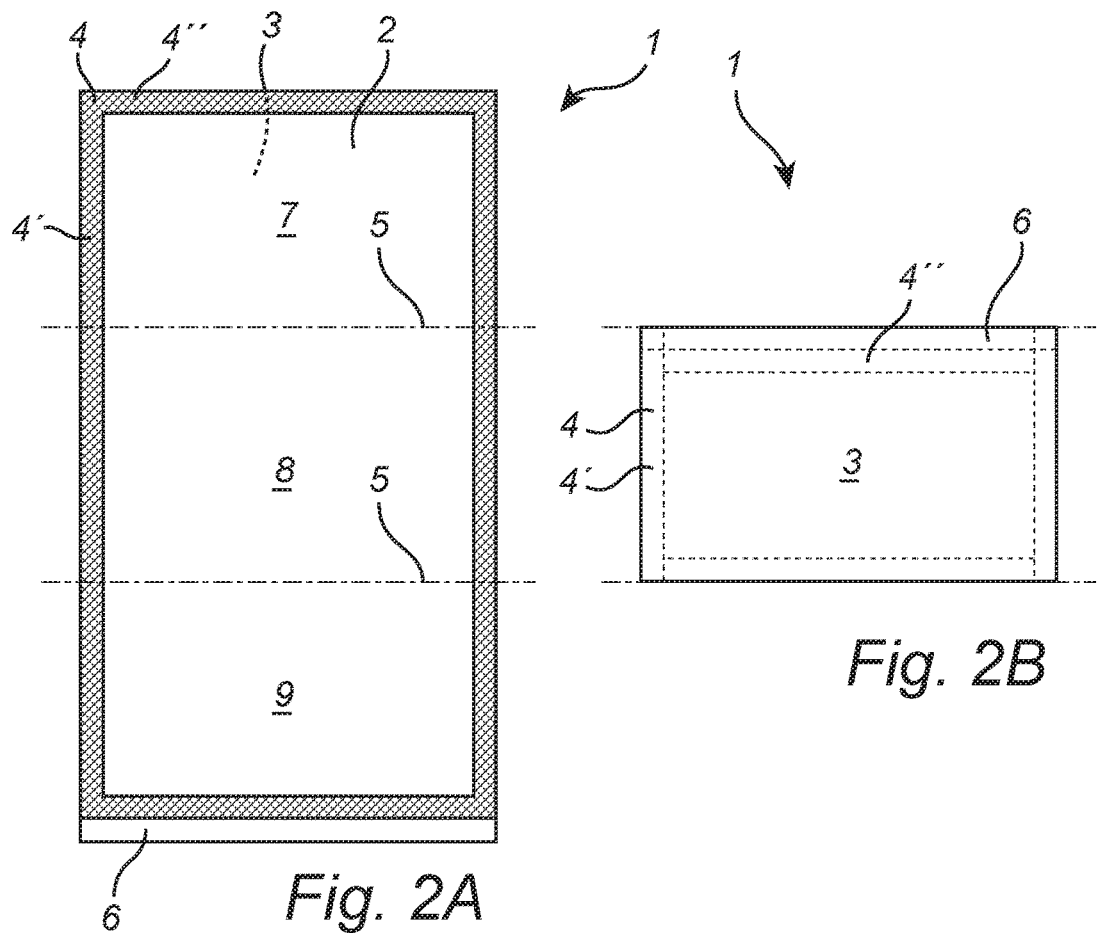
Fig. 2A
Fig. 2B
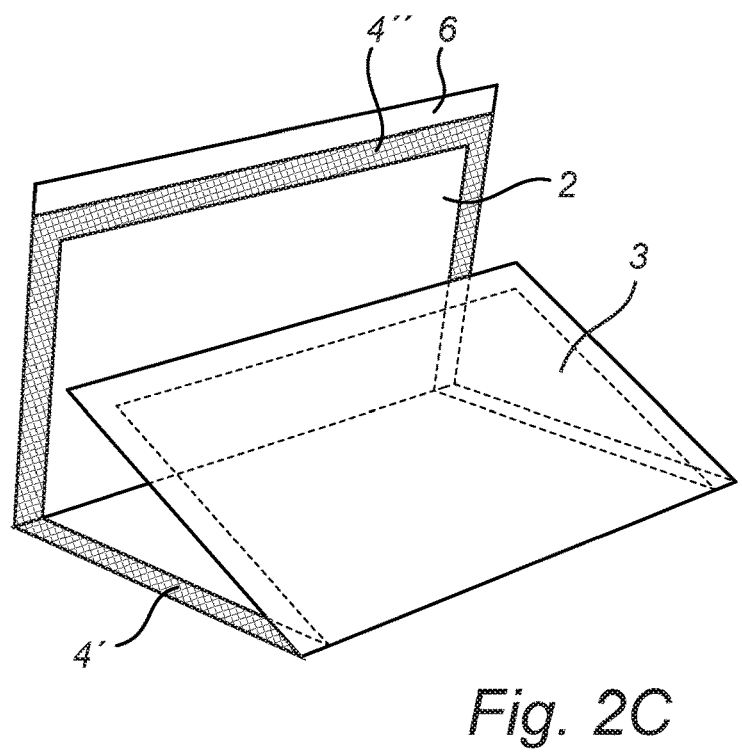
Fig. 2C

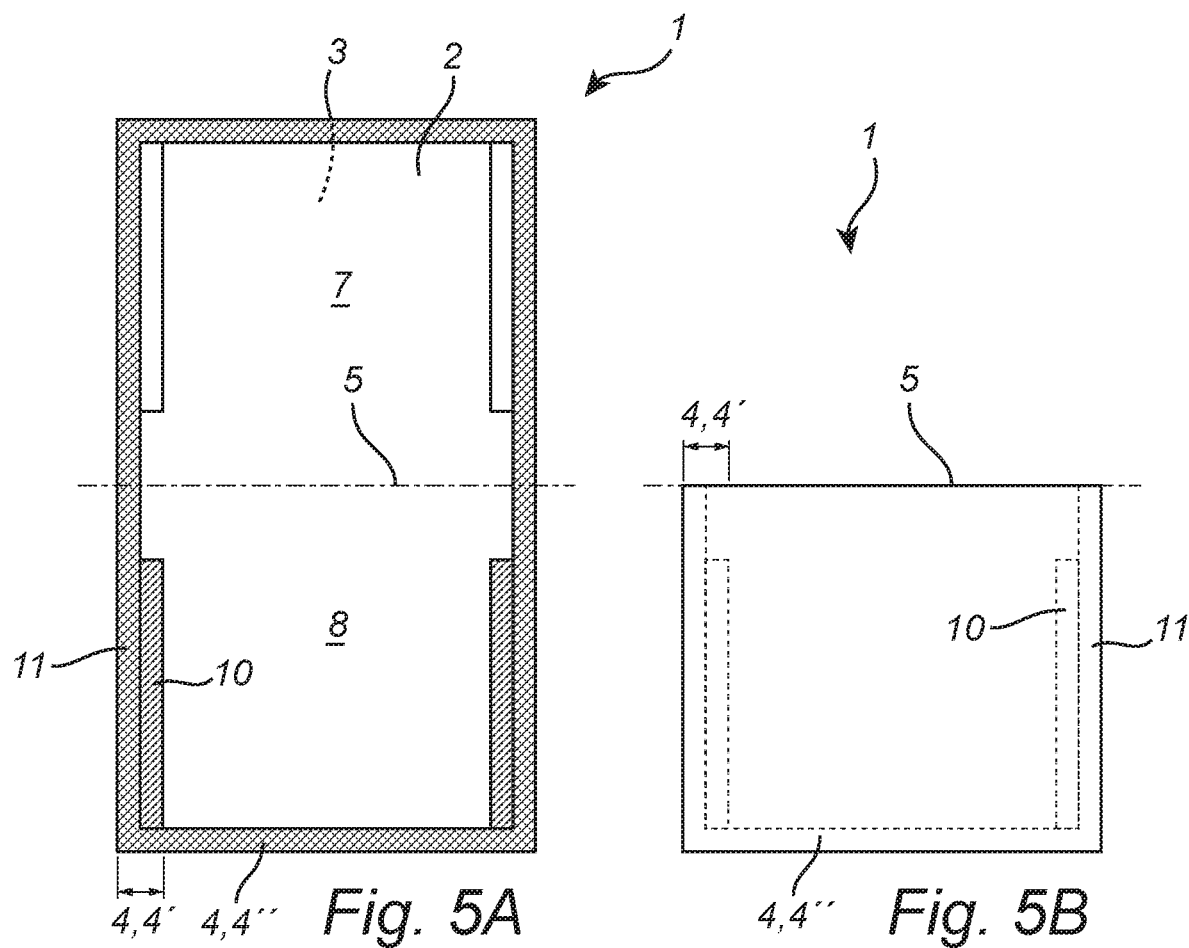

PACKAGING UNIT FOR HYGIENE ARTICLES

CROSS REFERENCE TO RELATED APPLICATIONS

This is the U.S. National Phase application of PCT/SE2017/050843, filed Aug. 22, 2017, the disclosure of which is incorporated herein by reference in its entirety for all purposes.

TECHNICAL FIELD

The present disclosure pertains to a packaging unit for hygiene articles, such as absorbent articles, the packaging unit being formed from a sheet of material.

BACKGROUND

Disposable hygiene articles, such as sanitary napkins and panty liners, are normally packaged individually in e.g. an easy wrap or a single wrap. Individual packages facilitate hygienic carrying of single articles for future use, e.g. in a handbag. Further, the packaging units are often used both as a means for packaging an unused article and for disposal of the used article.

It is desirable that used articles of this kind can be disposed of discretely and hygienically. This may be particularly important when the user lacks possibility to dispose of the used article immediately after the used article has been replaced, e.g. when there is no waste bin available in the toilet area. In this case, the user may need to put the used article in e.g. the handbag or backpack, which requires that the package is tightly sealed to avoid staining and odour.

WO2013162430A1 discloses a sheet of material for individually wrapping absorbent articles. The sheet of material may be reused for wrapping the used article and may be resealed using the resealable pressure sensitive adhesive provided for both the initial sealing and the resealing of the sheet. The pressure sensitive adhesive provided for such a reclosable package is adapted to provide, and is a compromise between, an initial easily openable seal and a strong reseal.

SUMMARY

The present disclosure relates to a packaging unit and a method for producing a packaging unit as described below, collectively providing a new and improved packaging unit for hygiene articles and a method of forming such packaging unit.

Thus, a packaging unit for hygiene articles, the packaging unit being formed from a sheet of material having an inner surface and an outer surface, said inner surface comprising an edge zone, said sheet having at least one folding axis, said folding axis dividing said sheet into a first region and a second region, said sheet may be folded along said folding axes with said first and second regions in an overlapping configuration, and wherein at least a part of said edge zone is provided with microencapsulated adhesive.

The method of forming a packaging unit for hygiene articles, the packaging unit being formed from a sheet of material having an inner surface and an outer surface, said inner surface comprising an edge zone, said sheet having at least one folding axis, said folding axis dividing said sheet into a first region and a second region, said sheet may be folded along said folding axes with said first and second regions in an overlapping configuration, the method comprising at least the step of providing microencapsulated adhesive on at least a part of said edge zone.

The present disclosure provides a packaging unit which can be used both for packaging of a new hygiene article and for safe and hygienic disposal of a used hygiene article. The packaging unit provides for a possibility of forming an easily openable package for a new article and a tightly sealed package for a used article, thus eliminating the risk of staining and odour from a used article.

Benefits of encapsulation of adhesives are also the possibility to provide high reclosability (closure rate) of the packaging unit due to a possibility to use strong or different types of adhesives in the microcapsules compared when using reclosable glues for both the first sealing and resealing of the packaging unit.

As used herein, the term "inner surface" refers to the surface of the packaging unit facing the product positioned inside the packaging unit, and the term "outer surface" refers to the surface opposite to the inner surface, i.e. the surface facing the ambient.

By the term "edge zone" is meant the portion of the packaging unit adjacent to the edges of the packaging unit. The width of an edge zone may be varied.

The term "inner edge portion" refers to the portion of the edge zone positioned towards the centreline of the packaging unit.

The term "outer edge portion" refers to the portion of the edge zone positioned towards the edge of the packaging unit.

By the term "single ply" is meant a packaging unit comprising a single ply of a coherent material. The examples of a single ply packaging unit may be a plastic film, such as a polyethylene film, a nonwoven material, a metallic foil or the like. A single ply material may be a non-homogenous material such as a plastic film material comprising integrated layers or a nonwoven material having varying fibre composition in different parts of the material. A single ply material as used herein does not comprise materials having separable layers.

By the term "laminate" is meant a packaging unit comprising at least two united separable layers of material that can be same or different. In the context of the present invention, the laminate may for example be constituted of two separable layers of plastic film, a film and nonwoven, two layers of nonwoven or the like.

As used herein "hygiene article" means an article selected from absorbent articles and wound care articles.

As used herein "absorbent article" means an article selected from a sanitary napkin, a panty liner, an incontinence pad, an incontinence diaper, a belted diaper, baby diaper or tampon. An absorbent article may comprise at least a topsheet and a backsheet. An absorbent article may in addition comprise a core of superabsorbents, cellulose fibers or a mixture of these provided between the topsheet and the backsheet.

The present invention provides a packaging unit for hygiene articles and a method of forming a packaging unit, which substantially eliminate the drawbacks of the packaging unit discussed above.

DETAILED DESCRIPTION OF PARTICULAR EMBODIMENTS

Sheet of Material

The geometrical shape of the sheet of material may vary depending on the type of hygiene article to be packaged. The sheet may be circular, triangular, square, rectangular, or any other shape suitable for the hygiene article to be packaged. It is desirable, however, that the sheet has at least one symmetry axis.

As mentioned above, the packaging unit comprises at least one folding axis. The number of folding axes may vary depending on how the packaging unit is intended to be folded. The packaging unit may comprise between one and three folding axes.

The prevailing shape of the sheet of material for forming a packaging unit is square or rectangular. Such a sheet according to the present disclosure has side edges, referred to herein as longitudinal edges, transverse edges and corner portions, and wherein the edge zones of the first and second regions of the sheet of material may be arranged along the longitudinal edges.

One of the most common folding patterns for individually wrapped hygiene products is so called e-folding. In this case the sheet has two folding axes, dividing the sheet into a first region, a second region and a third region. The packaging unit may then be formed, wherein the sheet is folded along the folding axes with the first, second and third regions in an overlapping configuration.

The sheet for forming a packaging unit may be a single ply sheet of any suitable material known to the person skilled in the art, such as film or nonwoven of polyethylene and/or polypropylene. The sheet may also be a laminate comprising at least two distinct layers. Laminates suitable for packaging of hygiene articles are assumed to be known to the person skilled in the art, and are not in any way limiting for the present invention.

If desired, the sheet for forming a packaging unit according to the present disclosure may be opaque in order to disguise the contents of the packaging unit. This is particularly important if the used article wrapped into the packaging unit of the present disclosure cannot be disposed of immediately after replacement. Further, the sheet may comprise print, which may be beneficial for attracting the user's attention and improving the user's mood.

It is conceivable that the sheet for forming a packaging unit according to the present disclosure may be stretchable or expandable. This may be advantageous if the hygiene article is greatly deformed during use, and may thus be difficult to wrap without deforming the packaging unit.

The sheet of material may be treated with a release agent, such as silicone. The agent may be added to selected parts only, such as the edge zone, or part of the edge zone, such as the inner edge portion.

Microencapsulated Adhesive

The microencapsulated adhesive is enclosed from surrounding media. The enclosure is achieved through complete encapsulation of a non-compatible fluid, by non-permeable or semi-permeable walls, or through the incorporation of the adhesive in an insoluble matrix such as in a cross-linked alginate-based microsphere. The choice of microencapsulation means depends on the hydrophilic/lipophilic nature of the adhesive as well as its sensitivity to exposure to media which can cause the additive to lose its function (sensitivity to pH changes, oxidation, discoloration etc.). The enclosure may be achieved through complete encapsulation of a non-compatible fluid by non-permeable or semi-permeable water-insoluble walls, or through the incorporation of the additive in a water-insoluble matrix.

Microencapsulation may be done through emulsion polymerization in oil-in-water emulsions to create emulsions, dispersions or dry powders. Typical shell materials include polymeric, melamine, and silica based compositions. The microcapsule material may be a composite of silicone and melamine polymers. The microcapsule material may be water-insoluble at 20° C.

Examples of suppliers providing encapsulated adhesives are Microteklabs, LipotechnologiesNantage and Encapsys.

The size of the microcapsules may be at least 0.1 µm, or at least 1 µm, or at least 3 µm, or at least 10 µm and may be below 100 µm, or below 70 µm, or below 30 µm. The size of the microcapsules may be 0.1-100 µm, 1-100 µm, or 1-70 µm, or 1-30 µm.

The adhesive is microencapsulated and may be added to the sheet of material as an emulsion, a dispersion or as a powder. The concentration of microcapsules in the resulting composition and the amount of composition applied to the sheet may be determined by the skilled man in the art by routine experiments and formulated for each specific use. The concentration of microcapsules depends on the used adhesive and the desired adhesive strength.

The concentration of microcapsules on the sheet of material depends on the type of adhesive and the desired adhesive strength. The concentration of microencapsulated adhesive on the sheet of material may be at least 0.1 g/m$^2$, or at least 0.5 g/m$^2$ or at least 1 g/m$^2$ and below 30 g/m$^2$, or below 25 g/m$^2$ or below 20 g/m$^2$. The concentration of microcapsules on the sheet of material may be 0.1-30 g/m$^2$, or 0.5-30 g/m$^2$ or 1-20 g/m$^2$.

The microencapsulated adhesive may be applied by a spraying, slot coating or an extrusion technique or by printing on the sheet of material. By printing we herein mean any kind of precise application of a fluid to form a coating or a dry layer on a substrate. By precise we mean that the medium will be placed in designated areas on the substrate, rather than in a poorly controlled fashion such as when using a spraying or extrusion technique. The print may be of contact type such as selected from flexoprint, screen print, offset, rotogravure or of non-contact type, such as selected from digital inkjet which may be continuous or drop on demand, intermittent drop formation by piezo, heat activated or other type of technology. The composition of microencapsulated adhesive may be applied by an in-line synchronized print technique, allowing for an exact placement of the composition.

In-line synchronized printing may be incorporated as steps in the process of manufacturing the packaging unit, or may be in-line synchronized printed before introduction of the absorbent article.

The composition of microencapsulated adhesive may be applied in selected areas as desired, and in any desired pattern.

The sheet of material may be substantially rectangular. The sheet comprises longitudinal edges, transverse edges and corner portions, and wherein said edge zone of said first and second regions of said sheet of material may be arranged along said longitudinal edges and provided with microencapsulated adhesive.

The sheet of material comprises transverse edge zones and wherein at least a portion of one of said transverse edge zones may be provided with microencapsulated adhesive for secure sealing of the sheet of material around a used article.

The width of the microencapsulated adhesive-covered edge portions may be varied depending on the adhesive strength desired. The wider the adhesive-covered edge zones, the stronger the sealing. The width of the adhesive-covered edge portions may be same or different in the different regions. The width of the adhesive-covered edge portions may be 0.3-30 mm, or 0.3-20 mm, or 0.5-15 mm.

The length of the adhesive-covered edge portions in each region may be equal to the length of each region, or may be 0.1-5 millimetres shorter than the length of each region. In an embodiment, preferably, the length of the adhesive-covered edge portions in each region is equal to the length of each region.

The microencapsulated adhesive may be applied on 0.5-100% of the area of the sheet of material, or 10-50%, or 15-40%, or as 20-35%.

A suitable microencapsulated adhesive to be used with the packaging unit of the present invention is a non-reclosable adhesive.

Characteristics of non-reclosable adhesives for post-use sealing are high elasticity and long open times. After closure the seal made with such a glue will not open without breaking the seal. Examples of manufacturers of non-reclosable adhesives suitable for personal care products are Savaré, HB Fuller, Henkel, Bostik and Colquimica.

For a reclosable adhesive to be useful as a permanent or semi-permanent seal for wrapping a used hygiene product for disposal purposes it needs to have sufficiently high adhesive strength. For the post-use seal to be considered satisfactory at least 50% of a statistical take-out of wrapped products should stay sealed (closure rate) for 1 h after closure by external force according to the test method "Method for measuring reclosability" as described in WO2015060770A1.

First Sealing of the Package

The packaging unit for hygiene articles is formed from a sheet of material having an inner surface and an outer surface, the inner surface comprising an edge zone, the sheet having at least one folding axis dividing the sheet into a first region and a second region, the sheet may be folded along the folding axes with the first and second regions in an overlapping configuration. The edge zone is at least partly provided with microencapsulated adhesive.

The packaging unit may be wrapped around and enclose a hygiene article and sealed by a first sealing means. The first sealing means may be selected from mechanical, heat or an adhesive. The microencapsulated adhesive may be provided on the sheet of material for a subsequent, second, and later sealing of the sheet of material when it is used for wrapping a used article.

Mechanical sealing is known to the skilled man in the art and may be achieved by and selected from embossing, ultrasonic welding and hook and loop fasteners, as known to the skilled man in the art.

Heat sealing may be achieved by bringing material surfaces of at least one thermoplastic material into contact at an elevated temperature to form a bond between the surfaces in a desired pattern of contact points, as known to skilled man in the art.

The adhesive used for the first sealing means may be an easily openable adhesive having an adhesive strength between 0.3 and 3.5 N. Such adhesive for the first sealing means may be a reclosable or a non-reclosable adhesive as known to the skilled man in the art.

Pressure-sensitive reclosable adhesive may be used with the packaging unit as the first sealing means and may be one which has a very high self-adhesion but which can be readily separated or released from other materials, such as plastic materials or paper which has been treated with a release agent.

A reclosable adhesive with sufficiently low adhesive strength may be needed for it to be opened easily when used for the first and initial sealing of the wrap of the unused product. By low adhesive strength we typically mean an opening force of a glued seal of less than 0.3 N in a first opening area (pull 1) of the wrap part forming a lid, and less than 2 N in a second opening area (pull 2) of the wrap part forming a pocket, as further described in test method "Method for measuring the adhesive force of the packaging unit" in patent application WO2015/060770 A1. By high adhesive strength we typically mean a first opening force (pull 1) higher than 0.7 N and a second opening force (pull 2) higher than 3.5 N.

Examples of manufacturers of reclosable adhesives suitable for personal care products are Savaré, HB Fuller, Henkel, Bostik and Colquimica.

The width of the adhesive-covered edge portions may be varied depending on the adhesive strength desired. The wider the adhesive-covered edge zones, the stronger the sealing. The width of the adhesive-covered edge portions may be same or different in the different regions.

The length of the adhesive-covered edge portions in each region may be equal to the length of each region, or may be 0.1-5 millimetres shorter than the length of each region. In an embodiment, preferably, the length of the adhesive-covered edge portions in each region is equal to the length of each region.

At least one of the transverse edges of the packaging unit according to the present disclosure may be provided with a first adhesive. To facilitate opening a transverse edge zone or at least one of the corner portions may be free from adhesive such that a gripping tab is formed.

The sheet of material may be of substantially rectangular shape and comprise longitudinal edges, transverse edges and corner portions, wherein an edge zone of the first and second regions of the sheet of material may be arranged along said longitudinal edges.

The edge zone may comprise an inner edge portion and an outer edge portion and at least one of said inner edge portion and said outer edge portion of said edge zone may be provided with microencapsulated adhesive and at least one of said inner edge portion and said outer edge portion of said edge zone is being provided with a first sealing means. The outer edge portion of said edge zone may be provided with microencapsulated adhesive and the inner edge portion of said edge zone may be provided with a first sealing means.

BRIEF DESCRIPTION OF THE DRAWINGS

The disclosure will now be described by way of example, referring to the drawings.

FIG. 1A-1C shows the edge sealing pattern of a packaging unit having one folding axis in an open and a folded state.

FIG. 2A-2C shows the edge sealing pattern of a packaging unit having two folding axes in an open and a folded state.

FIG. 5A-5B shows the edge sealing pattern of a packaging unit having one folding axis in an open and a folded state.

FIG. 1A-1C depicts a packaging unit 1 for hygiene articles according to the present disclosure. The packaging unit is formed from a sheet of material having an inner surface 2 and an outer surface 3, the inner surface has an edge zone 4 having a longitudinal edge portion 4' and a transverse edge portion 4" and is provided with microencapsulated adhesive on at least a portion thereof such as along the longitudinal edge portion 4'. The sheet has a folding axis 5, wherein the folding axis 5 divides the sheet into a first region 7 and a second region 8. The sheet of material may further have a transverse edge portion 6 free from adhesive forming a grip tab.

FIG. 2A-2C depicts a packaging unit 1 for hygiene articles according to the present disclosure. The packaging unit is formed from a sheet of material having an inner surface 2 and an outer surface 3, the inner surface has an edge zone 4 having a longitudinal edge portion 4' and a transverse edge portion 4". The sheet has two folding axes 5, wherein the folding axes 5 divides the sheet into a first region 7, a second region 8 and a third region 9. The edge zone 4 is provided with microencapsulated adhesive on at least a part thereof, such as along the longitudinal edge portions 4' of the first 7 and third 9 regions. The sheet of material has a transverse edge portion 6 free from adhesive forming a grip tab. The folded packaging in FIG. 2B is provided with a first ultrasonic seal along the inner edge portion of the edge zone 4.

FIG. 3A-3B depicts a packaging unit 1 for hygiene articles according to the present disclosure. The packaging unit is formed from a sheet of material having an inner surface 2 and an outer surface 3, the inner surface has an edge zone 4 having a longitudinal edge portion 4' and a transverse edge portion 4". The sheet has a folding axis 5, wherein the folding axis 5 divides the sheet into a first region 7 and a second region 8. The edge zone 4 of the second region 8 has an inner edge portion 10 and an outer edge portion 11 along its longitudinal edge portion 4' and transverse edge portion 4". The outer edge portion 11 is provided with microencapsulated reclosable adhesive.

Figure 3A:
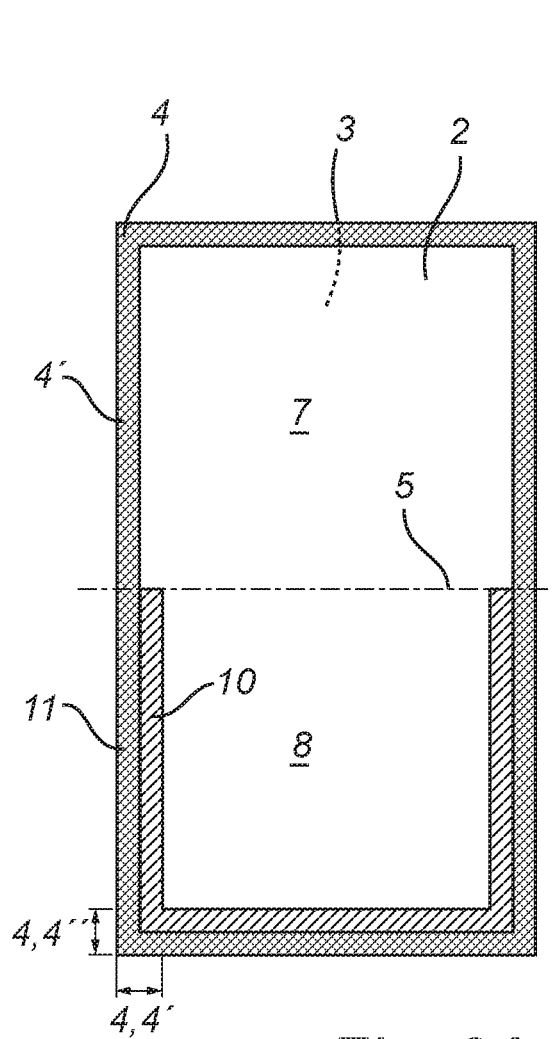
FIG. 3A-3B shows the edge sealing pattern of a packaging unit having one folding axis in an open and a folded state.
Figure 3B:
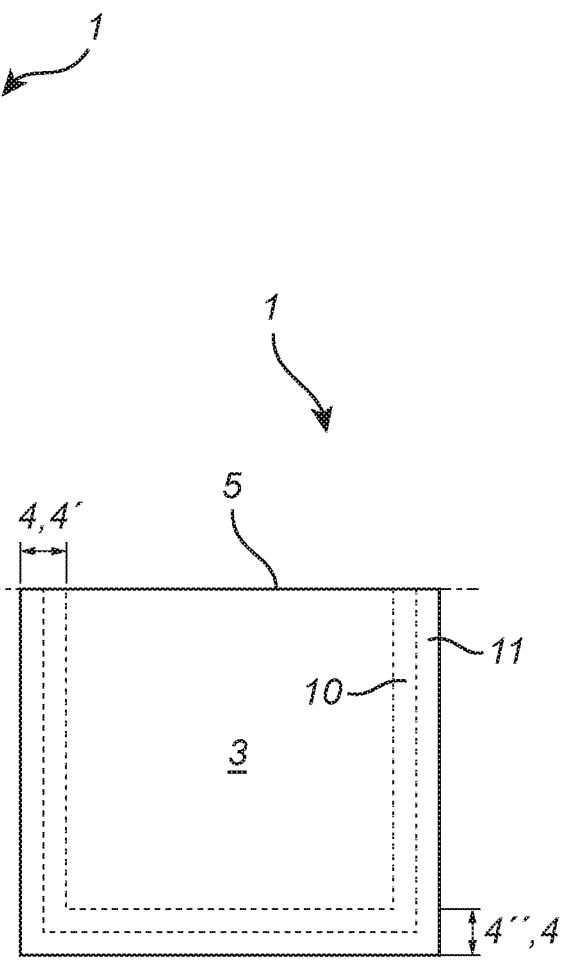

The folded packaging in FIG. 3B is sealed with heat embossing along the inner edge portion 10.

Figure 4:
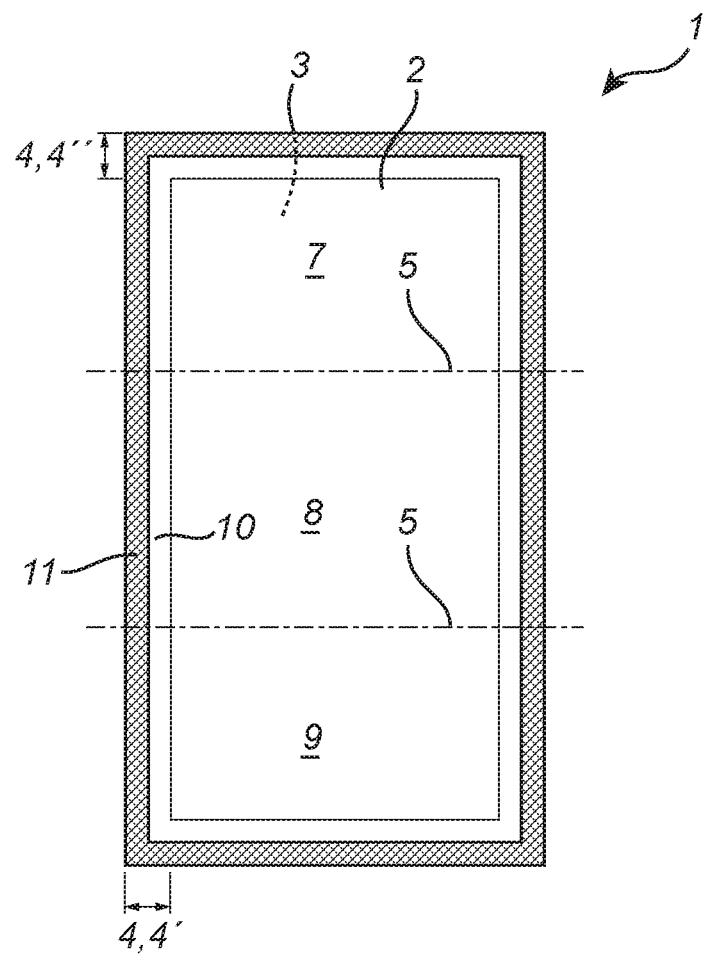
FIG. 4 shows the edge sealing pattern of a packaging unit in an open state.

FIG. 4 depicts a packaging unit 1 for hygiene articles according to the present disclosure. The packaging unit is formed from a sheet of material having an inner surface 2 and an outer surface 3, the inner surface has an edge zone 4 having a longitudinal edge portion 4' and a transverse edge portion 4". The sheet has two folding axes 5, wherein the folding axis 5 divides the sheet into a first region 7, a second region 8 and a third region 9. The edge zone 4 has an inner edge portion 10 provided with reclosable adhesive and an outer edge portion 11 along its longitudinal 4' and transverse edge portions 4" provided with microencapsulated adhesive.

FIG. 5A-5B depicts a packaging unit 1 for hygiene articles according to the present disclosure. The packaging unit is formed from a sheet of material having an inner surface 2 and an outer surface 3, the inner surface has an edge zone 4 having a longitudinal edge portion 4' and a transverse edge portion 4". The sheet has a folding axis 5, wherein the folding axis 5 divides the sheet into a first region 7 and a second region 8. The longitudinal edge zone 4' of the first 7 and second 8 regions has an inner edge portion 10 partly extending along the longitudinal length of the sheet of material and an outer edge portion 11 substantially extending along the whole longitudinal length of the sheet and is provided with reclosable microencapsulated adhesive. The folded packaging in FIG. 5B is sealed by adhesive being provided on the inner edge portion 10 of the second region 8. The inner edge portion 10 of the first region 7 is provided with release agent.

EXAMPLES

Example 1

A polymeric film suitable as wrap for hygiene products was used in a converting operation including the making of personal care products for hygiene use. In the converting operation, an encapsulated reclosable adhesive (THL 2181E, Bostik) was applied by slot coating at an amount of 12 g/m² onto the polymeric wrap film on the outer edge portion of the edge zone as seen in FIG. 5A, after which the wrap material was sealed around the hygiene products by means of applying a reclosable adhesive (PT 230, Savaré) of low adhesive strength of 0.2 N (pull 1) and 1.6 N (pull 2) at an amount of 15 g/m² on the inner edge portion of the edge zone as shown in FIG. 5A. The wrap was opened and was used to enclose a used hygiene product and sealed through activation of the encapsulated adhesive by external force. After activation of the encapsulated adhesive by external force resulting adhesive strengths of 0.7 N (open 1) and 4.0 N (open 2) were obtained. The high adhesive strength of the post-use glue seal gave a closure rate of more than 85% after 1 h when used for sealing the wrap film around a hygiene product after usage.

Example 2

A polymeric film suitable as wrap for hygiene products was used in a converting operation including the making of personal care products for hygiene use. In the converting operation, an encapsulated adhesive (Technomelt DM 6170, Henkel) was applied by slot coating at an amount of 6 g/m² onto the outer edge portion of the edge zone of the polymeric wrap film as seen in FIG. 2A after which the wrap material was sealed around the hygiene products by means of ultrasonic welding on the inner edge portion of the edge zone. The wrap was opened and used to enclose a used hygiene product and sealed through activation of the encapsulated adhesive by external force. The activated adhesive resulted in a high closure rate of more than 90% after 1 h for wrapped and sealed hygiene products after usage.

Example 3

A film/nonwoven laminate suitable as wrap for hygiene products was used in a converting operation including the making of personal care products for hygiene use. 13 g/m² of an encapsulated reclosable adhesive (PT 234, Savaré) was in the converting operation applied by slot coating onto the polymeric wrap film as disclosed in FIG. 3A, after which the wrap material was sealed around the hygiene products by means of heat embossing. The wrap was opened and wrapped around a used product and the encapsulated adhesive was activated by external force. The adhesive strength of the post-use seal gave a high closure rate of more than 75% after 1 h when used for sealing the wrap film around a hygiene product after usage.

Example 4

A polymeric web material suitable as wrap for hygiene products was used in a converting operation including the making of personal care products for hygiene use. In the converting operation, an encapsulated adhesive (FullCare 8400, HB Fuller) was applied by slot coating on the outer edge portion of the edge zone at an amount of 2 g/m² onto the polymeric wrap film as shown in FIG. 5A after which the wrap material was sealed around the hygiene products by means of reclosable adhesive (PT 230, Savaré) of low adhesive strength of 0.2 N (pull 1) and 1.6 N (pull 2) at an amount of 16 g/m² applied on a part of the inner edge portion of the edge zone as seen in FIG. 5A. The wrap was opened and used to enclose a used hygiene product and sealed through activation of the encapsulated adhesive by external force. The activated adhesive resulted in a high closure rate of more than 95% after 1 h for wrapped and sealed hygiene products after usage.

The invention claimed is:

1. A packaging unit for hygiene articles,
   said packaging unit being formed from a sheet of material having an inner surface and an outer surface, said inner surface comprising an edge zone, said sheet having at least one folding axis, said folding axis dividing said sheet into a first region and a second region, said sheet being folded along said folding axes with said first and second regions in an overlapping configuration,
   wherein at least a part of said edge zone is provided with microencapsulated adhesive,
   wherein said edge zone includes an inner edge portion and an outer edge portion that separates said inner edge portion from a peripheral edge of said packaging unit, and
   wherein one of said inner edge portion and said outer edge portion is provided with the microencapsulated adhesive and the other of said inner edge portion and said outer edge portion is provided with a first sealing means, said first sealing means being different from the microencapsulated adhesive such that one may be used to initially seal said packaging unit with a new hygiene article therein and another may be used to make a subsequent closure and seal of said packaging unit for wrapping and transporting a used hygiene article therein.

2. The packaging unit according to claim 1, wherein the microencapsulated adhesive is applied on 10-50% of the area of the sheet of material.

3. The packaging unit according to claim 1, wherein the microencapsulated adhesive is distributed over substantially the whole inner surface of the sheet of material.

4. The packaging unit according to claim 1, wherein 0.1-30 g/m² of microencapsulated adhesive is added to the sheet of material.

5. The packaging unit according to claim 1, wherein said first sealing means is selected from mechanical, heat and adhesive.

6. The packaging unit according to claim 5, wherein the adhesive of the first sealing means is an adhesive having an adhesive strength between 0.3 and 3.5 N.

7. The packaging unit according to claim 5, wherein the mechanical sealing means is selected from the group consisting of embossing, ultrasonic welding and hook and loop fasteners.

8. The packaging unit according to claim 1, wherein said packaging unit is reclosable by said microencapsulated adhesive.

9. The packaging unit according to claim 1, wherein said sheet of material is substantially rectangular and comprises longitudinal edges, transverse edges and corner portions, wherein said edge zone of said first and second regions of said sheet of material is arranged along said longitudinal edges.

10. The packaging unit according to claim 1, wherein said sheet of material comprises transverse edge zones and wherein at least a portion of one of said transverse edge zones is provided with microencapsulated adhesive.

11. The packaging unit according to claim 1, wherein the outer edge portion of said edge zone is provided with the microencapsulated adhesive, and wherein the inner edge portion of said edge zone is provided with the first sealing means.

12. The packaging unit according to claim 1, wherein said sheet has two folding axes, dividing said sheet into a first region, a second region and a third region).

13. The packaging unit according to claim 12, wherein said sheet is folded along said folding axes with said first, second and third regions in an overlapping configuration.

14. The packaging unit according to claim 1, wherein said packaging unit is for individually wrapping an absorbent article.

15. The packaging unit according to claim 1, wherein the packaging unit enclose an absorbent article comprising at least a topsheet and a backsheet.

16. The packaging unit according to claim 1, wherein the sheet of material forming said packaging unit is a single ply material which does not comprise separable layers.

17. The packaging unit according to claim 16, wherein the singly ply material is a polymeric film.

18. The packaging unit according to claim 1, wherein the sheet of material also comprises a transverse edge zone which is free from adhesive to thereby form a grip tab on said packaging unit.

* * * * *